United States Patent [19]

Wiezer et al.

[11] 4,319,030

[45] Mar. 9, 1982

[54] ALKYLATED DIAZA-SPIRODECANES

[75] Inventors: Hartmut Wiezer, Gersthofen; Gerhard Pfahler, Augsburg; Harald Häberlein; Günther Nowy, both of Gersthofen, all of Fed. Rep. of Germany

[73] Assignee: Hoechst Aktiengesellschaft, Frankfurt am Main, Fed. Rep. of Germany

[21] Appl. No.: 178,927

[22] Filed: Aug. 18, 1980

[30] Foreign Application Priority Data

Aug. 21, 1979 [DE] Fed. Rep. of Germany ....... 2933732

[51] Int. Cl.$^3$ ............................................ C07D 405/04
[52] U.S. Cl. ......................................... 546/19; 546/20
[58] Field of Search ................................... 546/19, 20; 260/239.3 R

[56] References Cited

U.S. PATENT DOCUMENTS 3,708,473 1/1973 Collins .......................... 260/239.3 R
4,110,334 8/1978 Mayer et al. .......................... 546/19
4,220,773 9/1980 Wiezer et al. .......................... 546/19

OTHER PUBLICATIONS

March "Advanced Organic Chemistry: . . . ", (McGraw–Hill), (1968), p. 357.

*Primary Examiner*—Robert T. Bond
*Attorney, Agent, or Firm*—Connolly and Hutz

[57] ABSTRACT

The invention provides derivatives of polyalkyl-1-oxa-diaza-spirodecanes prepared from compounds of the formula

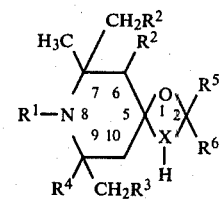

in which X is

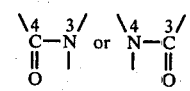

and mono- or dihalo-hydrocarbons by alkylation at the nitrogen atom of the 5-membered ring, and the salts thereof. The novel compounds are migration-resistant light stabilizers of low volatility for synthetic polymers.

1 Claim, No Drawings

ALKYLATED DIAZA-SPIRODECANES

The invention provides novel polyalkyl-diaza-spirodecanes, a process for the preparation thereof, and use thereof for stabilizing organic polymers against degradation induced by light and heat.

The novel polyalkyl-diaza-spirodecanes correspond to the formula (I)

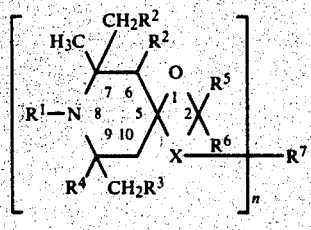

in which

X stands for a group of the formulae (II) or (III)

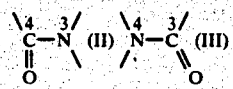

the indices 3 and 4 indicating the ring positions in the diaza-spirodecane system, and the free valency of the nitrogen atom producing the linkage with $R^7$;

$R^1$ is hydrogen, oxygen or $C_1$-$C_{12}$-alkyl, preferably hydrogen, oxygen or $C_1$-$C_4$-alkyl, especially hydrogen;

$R^2$ and $R^3$ either are identical and represent hydrogen or a $C_1$-$C_4$-alkyl group, preferably hydrogen or a methyl group, especially hydrogen; in which case $R^4$ is a methyl group; or $R^2$ is hydrogen or $C_1$-$C_5$-alkyl; and $R^3$ and $R^4$, together with the carbon atoms to which they are linked, form a $C_5$— or $C_6$—cycloalkyl group, or a group of the formula

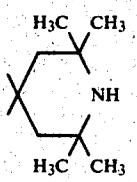

$R^5$ is hydrogen, $C_1$-$C_{30}$-alkyl, preferably $C_1$-$C_{18}$-alkyl, especially $C_1$-$C_5$-alkyl, unsubstituted phenyl or naphthyl, or phenyl or naphthyl substituted by chlorine or $C_1$-$C_4$-alkyl, preferably the first cited group, or an unsubstituted $C_7$-$C_{12}$-phenylalkyl group or a $C_7$-$C_{12}$-phenylalkyl group substituted by $C_1$-$C_4$-alkyl, preferably a benzyl group;

$R^6$ is hydrogen, $C_1$-$C_{30}$-alkyl, preferably $C_1$-$C_{18}$-alkyl, especially $C_1$-$C_{13}$-alkyl, an unsubstituted phenyl or naphthyl or a phenyl or naphthyl group substituted by chlorine or $C_1$-$C_4$-alkyl, preferably a phenyl group, an unsubstituted $C_7$-$C_{12}$-phenylalkyl group or such a phenylalkyl group substituted by $C_1$-$C_4$-alkyl, preferably a benzyl group;

$R^5$ and $R^6$, together with the carbon atom linking them, form an unsubstituted $C_5$-$C_{18}$-, preferably $C_5$-$C_{12}$-cycloalkyl group or such a cycloalkyl group substituted by up to four $C_1$-$C_4$-alkyl groups, preferably methyl groups, or a group of the formula

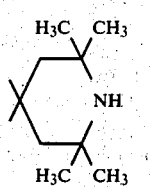

n is 1 or 2, and $R^7$, in the case where n is 1, is an alkyl group having from 1 to 30, preferably 1 to 18, especially 1 to 6, carbon atoms, an alkenyl group having from 2 to 18, preferably 3 to 12, especially 3 to 6, carbon atoms, a phenylalkyl group having from 7 to 18, preferably 7 to 10, especially 7, carbon atoms optionally substituted by a $C_1$-$C_4$-alkyl group, or a cycloalkyl group having from 5 to 12 carbon atoms; and in the case where n is 2, it is an alkylene group having from 2 to 30, preferably 2 to 18, especially 4 to 12, carbon atoms, an alkenylene group having from 2 to 30, preferably 2 to 18, especially 2 to 6, carbon atoms, or a phenylene-dialkylene group having from 8 to 18, preferably 8 to 10, especially 8, carbon atoms.

Furthermore included are the salts with non-oxidizing mineral acids, aliphatic sulfonic or phosphonic acids having from 1 to 30, preferably 1 to 18, carbon atoms, optionally alkylated aromatic sulfonic or phosphonic acids having from 6 to 25, preferably 6 to 18, carbon atoms; 1 to 3 alkyl groups having from 1 to 16 carbon atoms optionally being present; furthermore aliphatic mono- or dicarboxylic acids having from 2 to 34, preferably 2 to 18, carbon atoms, or aliphatic polycarboxylic acids having up to 4 carboxyl groups and a total of 16 carbon atoms, or aromatic carboxylic acids having up to 4 carboxyl groups and up to 25 carbon atoms, preferably up to 2 carboxyl groups and up to 19 carbon atoms.

Examples of polyalkyl-diaza-spirodecanes of the invention are:

(1) 2,2,3,7,7,9,9-hexamethyl-1-oxa-3,8-diaza-4-oxo-spiro-(4,5)-decane (2) 2,2,7,7,9,9-hexamethyl-3-ethyl-1-oxa-3,8-diaza-4-oxo-spiro-(4,5)-decane (3) 2,2,7,7,9,9-hexamethyl-3-propyl-1-oxa-3,8-diaza-4-oxo-spiro-(4,5)-decane (4) 2,2,7,7,9,9-hexamethyl-3-butyl-1-oxa-3,8-diaza-4-oxo-spiro-(4,5)-decane (5) 2,2,7,7,9,9-hexamethyl-3-pentyl-1-oxa-3,8-diaza-4-oxo-spiro-(4,5)-decane (6) 2,2,7,7,9,9-hexamethyl-3-hexyl-1-oxa-3,8-diaza-4-oxo-spiro-(4,5)-decane (7) 2,2,7,7,9,9-hexamethyl-3-nonyl-1-oxa-3,8-diaza-4-oxo-spiro-(4,5)-decane (8) 2,2,7,7,9,9-hexamethyl-3-dodecyl-1-oxa-3,8-diaza-4-oxo-spiro-(4,5)-decane (9) 2,2,7,7,9,9-hexamethyl-3-octadecyl-1-oxa-3,8-diaza-4-oxo-spiro-(4,5)-decane

(10) 2,2,7,7,9,9-hexamethyl-3-benzyl-1-oxa-3,8-diaza-4-oxo-spiro-(4,5)-decane

(11) 1',4'-bis-[2,2,7,7,9,9-hexamethyl-1-oxa-3,8-diaza-4-oxo-spiro-(4,5)-decyl-3-]-butane

(12) 1',6'-bis-[2,2,7,7,9,9-hexamethyl-1-oxa-3,8-diaza-4-oxo-spiro-(4,5)-decyl-3-]-hexane

(13) 1',10'-bis-[2,2,7,7,9,9-hexamethyl-1-oxa-3,8-diaza-4-oxo-spiro-(4,5)-decyl-3-]-decane

(14) 2,2,4,7,7,9,9-heptamethyl-1-oxa-3-oxo-4,8-diaza-spiro-(4,5)-decane

(15) 2,2,7,7,8,9,9-heptamethyl-4-butyl-1-oxa-3-oxo-4,8-diaza-spiro-(4,5)-decane

(16) 2,2,7,7,9,9-hexamethyl-4-ethyl-1-oxa-3-oxo-4,8-diaza-spiro-(4,5)-decane

(17) 2,2,7,7,9,9-hexamethyl-4-butyl-1-oxa-3-oxo-4,8-diaza-spiro-(4,5)-decane

(18) 2,2,7,7,9,9-hexamethyl-4-hexyl-1-oxa-3-oxo-4,8-diaza-spiro-(4,5)-decane

(19) 2,2,7,7,9,9-hexamethyl-4-dodecyl-1-oxa-3-oxo-4,8-diaza-spiro-(4,5)-decane

(20) 2,2,7,7,9,9-hexamethyl-4-octadecyl-1-oxa-3-oxo-4,8-diaza-spiro-(4,5)-decane

(21) 2,2,7,7,9,9-hexamethyl-4-benzyl-1-oxa-3-oxo-4,8-diaza-spiro-(4,5)-decane

(22) 1',6'-bis-[2,2,7,7,9,9-hexamethyl-1-oxa-3-oxo-4,8-diaza-spiro-(4,5)-decyl-4-]-hexane

(23) 1',10'-bis-[2,2,7,7,9,9-hexamethyl-1-oxa-3-oxo-4,8-diaza-spiro-(4,5)-decyl-4-]-decane

(24) 2,3,7,7,9,9-hexamethyl-2-ethyl-1-oxa-3,8-diaza-4-oxo-spiro-(4,5)-decane

(25) 2,7,7,9,9-pentamethyl-2-ethyl-3-hexyl-1-oxa-3,8-diaza-4-oxo-spiro-(4,5)-decane

(26) 2,7,7,9,9-pentamethyl-2-ethyl-3-octadecyl-1-oxa-3,8-diaza-4-oxo-spiro-(4,5)-decane

(27) 1',6'-bis-[2,7,7,9,9-pentamethyl-2-ethyl-1-oxa-3,8-diaza-4-oxo-spiro-(4,5)-decyl-3-]-hexane

(28) 2,4,7,7,9,9-hexamethyl-2-ethyl-1-oxa-3-oxo-4,8-diaza-spiro(4,5)-decane

(29) 2,7,7,9,9-pentamethyl-2-ethyl-4-hexyl-1-oxa-3-oxo-4,8-diaza-spiro-(4,5)-decane

(30) 2,7,7,9,9-pentamethyl-2-ethyl-4-benzyl-1-oxa-3-oxo-4,8-diaza-spiro-(4,5)-decane

(31) 1',4'-bis-[2,7,7,9,9-pentamethyl-2-ethyl-1-oxa-3-oxo-4,8-diaza-spiro-(4,5)-decyl-4-]-butane

(32) 2,3,7,7,9,9-hexamethyl-2-iso-propyl-1-oxa-3,8-diaza-4-oxo-spiro-(4,5)-decane

(33) 2,7,7,9,9-pentamethyl-2-propyl-3-ethyl-1-oxa-3,8-diaza-4-oxo-spiro-(4,5)-decane

(34) 1',4'-bis-[2,7,7,9,9-pentamethyl-2-propyl-1-oxa-3,8-diaza-4-oxo-spiro-(4,5)-decyl-3-]-butane

(35) 1',10'-bis-[2,7,7,9,9-pentamethyl-2-propyl-1-oxa-3,8-diaza-4-oxo-spiro-(4,5)-decyl-3-]-decane

(36) 2,7,7,9,9-pentamethyl-2-iso-propyl-4-hexyl-1-oxa-3-oxo-4,8-diaza-spiro-(4,5)-decane

(37) 2,4,7,7,9,9-hexamethyl-2-iso-propyl-1-oxa-3-oxo-4,8-diaza-spiro-(4,5)-decane

(38) 2,7,7,9,9-pentamethyl-2-iso-propyl-4-ethyl-1-oxa-3-oxo-4,8-diaza-spiro-(4,5)-decane

(39) 2,3,7,7,9,9-hexamethyl-2-iso-butyl-3,8-diaza-1-oxa-4-oxo-spiro-(4,5)-decane

(40) 2,7,7,9,9-pentamethyl-2-iso-butyl-3-ethyl-1-oxa-3,8diaza-4-oxo-spiro-(4,5)-decane

(41) 2,7,7,9,9-pentamethyl-2-iso-butyl-3-butyl-1-oxa-3,8-diaza-4-oxo-spiro-(4,5)-decane

(42) 2,7,7,9,9-pentamethyl-2-iso-butyl-3-hexyl-1-oxa-3,8-diaza-4-oxo-spiro-(4,5)-decane

(43) 2,7,7,9,9-pentamethyl-2-iso-butyl-3-nonyl-1-oxa-3,8-diaza-4-oxo-spiro-(4,5)-decane

(44) 2,7,7,9,9-pentamethyl-2-iso-butyl-3-octadecyl-1-oxa-3,8-diaza-4-oxo-spiro-(4,5)-decane

(45) 1',6'-bis-[2,7,7,9,9-pentamethyl-2-iso-butyl-1-oxa-3,8-diaza-4-oxo-spiro-(4,5)-decyl-3-]-hexane

(46) 1',10'-bis-[2,7,7,9,9-pentamethyl-2-iso-butyl-1-oxa-3,8-diaza-4-oxo-spiro-(4,5)-decyl-3-]-decane

(47) 2,7,7,9,9-pentamethyl-2-butyl-4-ethyl-1-oxa-3-oxo-4,8-diaza-spiro-(4,5)-decane

(48) 2,7,7,8,9,9-hexamethyl-2-iso-butyl-4-hexyl-1-oxa-3-oxo-4,8-diaza-spiro-(4,5)-decane

(49) 2,7,7,8,9,9-hexamethyl-2-iso-butyl-4-octadecyl-1-oxa-3-oxo-4,8-diaza-spiro-(4,5)-decane

(50) 2,7,7,9,9-pentamethyl-2-pentyl-3-benzyl-1-oxa-3,8-diaza-4-oxo-spiro-(4,5)-decane

(51) 2,4,7,7,9,9-hexamethyl-2-pentyl-1-oxa-3-oxo-4,8-diaza-spiro-(4,5)-decane

(52) 2,7,7,9,9-pentamethyl-2-pentyl-4-hexyl-1-oxa-3-oxo-4,8-diaza-spiro-(4,5)-decane

(53) 2,7,7,9,9-pentamethyl-2-pentyl-4-benzyl-1-oxa-3-oxo-4,8-diaza-spiro-(4,5)-decane

(54) 2,7,7,9,9-pentamethyl-2-pentyl-4-octadecyl-1-oxa-3-oxo-4,8-diaza-spiro-(4,5)-decane

(55) 1',4'-bis-[2,7,7,9,9-pentamethyl-2-pentyl-1-oxa-3-oxo-4,8-diaza-spiro-(4,5)-decyl-4-]-butane

(56) 2,7,7,9,9-pentamethyl-2-hexyl-3-nonyl-1-oxa-3,8-diaza-4-oxo-spiro-(4,5)-decane

(57) 2,4,7,7,9,9-hexamethyl-2-hexyl-1-oxa-3-oxo-4,8-diaza-spiro-(4,5)-decane

(58) 2,7,7,9,9-pentamethyl-2-hexyl-4-ethyl-1-oxa-3-oxo-4,8-diaza-spiro-(4,5)-decane

(59) 2,7,7,9,9-pentamethyl-2-hexyl-4-butyl-1-oxa-3-oxo-4,8-diaza-spiro-(4,5)-decane

(60) 2,7,7,9,9-pentamethyl-2,4-dihexyl-1-oxa-3-oxo-4,8-diaza-spiro-(4,5)-decane

(61) 1',4'-bis-[2,7,7,9,9-pentamethyl-2-hexyl-1-oxa-3-oxo-4,8-diaza-spiro-(4,5)-decyl-4-]-butane

(62) 1',6'-bis-[2,7,7,9,9-pentamethyl-2-hexyl-1-oxa-3-oxo-4,8-diaza-spiro-(4,5)-decyl-4-]-hexane

(63) 2,7,7,9,9-pentamethyl-2-hexyl-4-octadecyl-1-oxa-3-oxo-4,8-diaza-spiro-(4,5)-decane

(64) 2,7,7,9,9-pentamethyl-2-iso-hexyl-4-benzyl-1-oxa-3-oxo-4,8-diaza-spiro-(4,5)-decane

(65) 2,7,7,9,9-pentamethyl-2-nonyl-3-ethyl-1-oxa-3,8-diaza-4-oxo-spiro-(4,5)-decane

(66) 2,7,7,9,9-pentamethyl-2-nonyl-3-butyl-1-oxa-3,8-diaza-4-oxo-spiro-(4,5)-decane

(67) 2,7,7,9,9-pentamethyl-2-nonyl-3-hexyl-1-oxa-3,8-diaza-4-oxo-spiro-(4,5)-decane

(68) 2,7,7,9,9-pentamethyl-2-nonyl-3-octadecyl-1-oxa-3,8-diaza-4-oxo-spiro-(4,5)-decane

(69) 1',6'-bis-[2,7,7,9,9-pentamethyl-2-nonyl-1-oxa-3,8-diaza-4-oxo-spiro-(4,5)-decyl-3-]-hexane

(70) 2,3,7,7,9,9-hexamethyl-2-undecyl-1-oxa-3,8-diaza-4-oxo-spiro-(4,5)-decane

(71) 2,7,7,9,9-pentamethyl-2-undecyl-3-ethyl-1-oxa-3,8-diaza-4-oxo-spiro-(4,5)-decane

(72) 2,7,7,9,9-pentamethyl-2-undecyl-3-hexyl-1-oxa-3,8-diaza-4-oxo-spiro-(4,5)-decane

(73) 2,7,7,9,9-pentamethyl-2-undecyl-3-octadecyl-1-oxa-3,8-diaza-4-oxo-spiro-(4,5)-decane

(74) 2,7,7,9,9-pentamethyl-2-undecyl-3-benzyl-1-oxa-3,8-diaza-4-oxo-spiro-(4,5)-decane

(75) 2,7,7,9,9-pentamethyl-2-undecyl-3-cumylyl-1-oxa-3,8-diaza-4-oxo-spiro-(4,5)-decane

(76) 1',6'-bis-[2,7,7,9,9-pentamethyl-2-undecyl-1-oxa-3,8-diaza-4-oxo-spiro-(4,5)-decyl-3-]-hexane

(77) 1',10'-bis-[2,7,7,9,9-pentamethyl-2-undecyl-1-oxa-3,8-diaza-4-oxo-spiro-(4,5)-decyl-3-]-decane

(78) 2,7,7,9,9-pentamethyl-2-undecyl-1-oxa-3-oxo-4-ethyl-4,8-diaza-spiro-(4,5)-decane

(79) 2,7,7,9,9-pentamethyl-2-undecyl-1-oxa-3-oxo-4-benzyl-4,8-diaza-spiro-(4,5)-decane

(80) 2,7,7,9,9-pentamethyl-2-undecyl-1-oxa-3-oxo-4-octadecyl-4,8-diaza-spiro-(4,5)-decane

(81) 1',6'-bis-[2,7,7,9,9-pentamethyl-2-undecyl-1-oxa-3-oxo-4,8-diaza-spiro-(4,5)-decyl-4-]-hexane
(82) 2,3,7,7,9,9-hexamethyl-2-octadecyl-1-oxa-3,8-diaza-4-oxo-spiro-(4,5)-decane
(83) 2,7,7,9,9-pentamethyl-2-octadecyl-3-ethyl-1-oxa-3,8-diaza-4-oxo-spiro-(4,5)-decane
(84) 2,7,7,9,9-pentamethyl-2-octadecyl-3-hexyl-1-oxa-3,8-diaza-4-oxo-spiro-(4,5)-decane
(85) 2,7,7,9,9-pentamethyl-2,3-dioctadecyl-1-oxa-3,8-diaza-4-oxo-spiro-(4,5)-decane
(86) 1',6'-bis-[2,7,7,9,9-pentamethyl-2-octadecyl-1-oxa-3,8-diaza-4-oxo-spiro-(4,5)-decyl-3-]-hexane
(87) 1',10'-bis-[2-7,7,9,9-pentamethyl-2-octadecyl-1-oxa-3,8-diaza-4-oxo-spiro-(4,5)-decyl-3-]-decane
(88) 3,7,7,9,9-pentamethyl-2,2-diethyl-1-oxa-3,8-diaza-4-oxo-spiro-(4,5)-decane
(89) 7,7,9,9-tetramethyl-2,2,3-triethyl-1-oxa-3,8-diaza-4-oxo-spiro-(4,5)-decane
(90) 7,7,9,9-tetramethyl-2,2-diethyl-3-butyl-1-oxa-3,8-diaza-4-oxo-spiro-(4,5)-decane
(91) 7,7,9,9-tetramethyl-2,2-diethyl-3-hexyl-1-oxa-3,8-diaza-4-oxo-spiro-(4,5)-decane
(92) 7,7,9,9-tetramethyl-2,2-diethyl-3-benzyl-1-oxa-3,8-diaza-4-oxo-spiro-(4,5)-decane
(93) 1',6'-bis-[7,7,9,9-tetramethyl-2,2-diethyl-1-oxa-3,8-diaza-4-oxo-spiro-(4,5)-decyl-3-]-hexane
(94) 3,7,7,9,9-pentamethyl-2-ethyl-2-iso-butyl-1-oxa-3,8-diaza-4-oxo-spiro-(4,5)-decane
(95) 7,7,9,9-tetramethyl-2-ethyl-2-iso-butyl-3-hexyl-1-oxa-3,8-diaza-4-oxo-spiro-(4,5)-decane
(96) 7,7,9,9-tetramethyl-2-ethyl-2-iso-butyl-3-benzyl-1-oxa-3,8-diaza-4-oxo-spiro-(4,5)-decane
(97) 7,7,9,9-tetramethyl-2-ethyl-2-butyl-1-oxa-3-oxo-4-benzyl-4,8-diaza-spiro-(4,5)-decane
(98) 1',4'-bis-[7,7,9,9-tetramethyl-2-ethyl-2-butyl-1-oxa-3-oxo-4,8-diaza-spiro-(4,5)-decyl-4-]-butane
(99) 7,7,9,9-pentamethyl-2,2-dibutyl-4-benzyl-1-oxa-4,8-diaza-3-oxo-spiro-(4,5)-decane
(100) 7,7,9,9-tetramethyl-2,2-dipentyl-3-hexyl-1-oxa-3,8-diaza-4-oxo-spiro-(4,5)-decane
(101) 7,7,9,9-tetramethyl-2,2-dipentyl-3-octadecyl-1-oxa-3,8-diaza-4-oxo-spiro-(4,5)-decane
(102) 7,7,9,9-tetramethyl-2,2-dipentyl-3-benzyl-1-oxa-3,8-diaza-4-oxo-spiro-(4,5)-decane
(103) 1',4'-bis-[7,7,9,9-tetramethyl-2,2-dipentyl-1-oxa-3,8-diaza-4-oxo-spiro-(4,5)-decyl-3-]-butane
(104) 1',6'-bis-[7,7,9,9-tetramethyl-2,2-dipentyl-1-oxa-3,8-diaza-4-oxo-spiro-(4,5)-decyl-3-]-hexane
(105) 1',10'-bis-[7,7,9,9-tetramethyl-2,2-dipentyl-1-oxa-3,8-diaza-4-oxo-spiro-(4,5)-decyl-3-]-decane
(106) 7,7,9,9-tetramethyl-2,2-ditetradecyl-3-hexyl-1-oxa-3,8-diaza-4-oxo-spiro-(4,5)-decane
(107) 1',6'-bis-[7,7,9,9-tetramethyl-2,2-ditetradecyl-1-oxa-3,8-diaza-4-oxo-spiro-(4,5)-decyl-3-]-hexane
(108) 7,7,9,9-tetramethyl-2,2-dioctadecyl-3-benzyl-1-oxa-3,8-diaza-4-oxo-spiro-(4,5)-decane
(109) 7,7,9,9-tetramethyl-2,2-dioctadecyl-3-hexyl-1-oxa-3,8-diaza-4-oxo-spiro-(4,5)-decane
(110) 7,7,9,9-tetramethyl-2,2,3-trioctadecyl-1-oxa-3,8-diaza-4-oxo-spiro-(4,5)-decane
(111) 1',6'-bis-[7,7,9,9-tetramethyl-2,2-dioctadecyl-1-oxa-3,8-diaza-4-oxo-spiro-(4,5)-decyl-3-]-hexane
(112) 3,7,7,9,9-pentamethyl-2-phenyl-1-oxa-3,8-diaza-4-oxo-spiro-(4,5)-decane
(113) 7,7,9,9-tetramethyl-2-iso-propyl-4-ethyl-1-oxa-4,8-diaza-3-oxo-spiro-(4,5)-decane
(114) 7,7,9,9-tetramethyl-2-iso-hexyl-3-ethyl-1-oxa-3,8-diaza-4-oxo-spiro-(4,5)-decane
(115) 3,7,7,9,9-pentamethyl-2-nonyl-1-oxa-3,8-diaza-4-oxo-spiro-(4,5)-decane
(116) 7,7,9,9-tetramethyl-2-iso-nonyl-3-hexyl-1-oxa-3,8-diaza-4-oxo-spiro-(4,5)-decane
(117) 7,7,9,9-tetramethyl-2-iso-heptyl-3-octadecyl-1-oxa-3,8-diaza-4-oxo-spiro-(4,5)-decane
(118) 7,7,9,9-tetramethyl-2-undecyl-3-benzyl-1-oxa-3,8-diaza-4-oxo-spiro-(4,5)-decane
(119) 1',4'-bis-[7,7,9,9-tetramethyl-2-iso-nonyl-1-oxy-3,8-diaza-4-oxo-spiro-(4,5)-decyl-3-]-butane
(120) 4,7,7,9,9-pentamethyl-2-iso-butyl-1-oxa-3-oxo-4,8-diaza-spiro-(4,5)-decane
(121) 7,7,9,9-tetramethyl-2-iso-heptyl-1-oxa-4-ethyl-3-oxo-4,8-diaza-spiro-(4,5)-decane
(122) 1',5'-bis-[7,7,9,9-tetramethyl-2-iso-pentyl-1-oxa-3-oxo-4,8-diaza-spiro-(4,5)-decyl-4-]-pentane
(123) 2,2,4,4-tetramethyl-13-hexyl-7-oxa-3,13-diaza-14-oxo-dispiro-(5,1,4,2)-tetradecane
(124) 2,2,4,4-tetramethyl-13-ethyl-7-oxa-3,13-diaza-24-oxo-dispiro-(5,1,4,2)-tetradecane
(125) 2,2,4,4-tetramethyl-13-butyl-7-oxa-3,13-diaza-14-oxo-dispiro-(5,1,4,2)-tetradecane
(126) 2,2,4,4-tetramethyl-14-ethyl-7-oxa-3,14-diaza-15-oxo-dispiro-(5,1,5,2)-pentadecane
(127) 2,2,4,4-tetramethyl-14-butyl-7-oxa-3,14-diaza-15-oxo-dispiro-(5,1,5,2)-pentadecane
(128) 2,2,4,4-tetramethyl-14-hexyl-7-oxa-3,14-diaza-15-oxo-dispiro-(5,1,5,2)-pentadecane
(129) 2,2,4,4-tetramethyl-14-benzyl-7-oxa-3,14-diaza-15-oxo-dispiro-(5,1,5,2)-pentadecane
(130) 1',4'-bis-[2,2,4,4-tetramethyl-7-oxa-3,14-diaza-15-oxo-dispiro-(5,1,5,2)-pentadecyl-14]-butane
(131) 1',4'-bis-[2,2,4,4-tetramethyl-1-oxa-3,14-diaza-15-oxo-dispiro-(5,1,5,2)-pentadecyl-14]-butane
(132) 1',6'-bis-[2,2,4,4-tetramethyl-7-oxa-3,14-diaza-15-oxo-dispiro-(5,1,5,2)-pentadecyl-14]-hexane
(133) 2,2,4,4,10,12-hexamethyl-14-ethyl-7-oxa-3,14-diaza-15-oxo-dispiro-(5,1,5,2)-pentadecane
(134) 2,2,4,4,10,10,12,12-octamethyl-14-ethyl-7-oxa-3,14-diaza-15-oxo-dispiro-(5,1,5,2)-pentadecane
(135) 2,2,4,4,15-pentamethyl-7-oxa-3,15-diaza-14-oxo-dispiro-(5,1,5,2)-pentadecane
(136) 2,2,4,4-tetramethyl-15-hexyl-7-oxa-3,15-diaza-14-oxo-dispiro-(5,1,5,2)-pentadecane
(137) 2,2,4,4,20-pentamethyl-7-oxa-3,20-diaza-21-oxo-dispiro-(5,1,11,2)-heneicosane
(138) 2,2,4,4-tetramethyl-20-ethyl-7-oxa-3,20-diaza-21-oxo-dispiro-(5,1,11,2)-heneicosane
(139) 2,2,4,4-tetramethyl-20-iso-propyl-7-oxa-3,20-diaza-21-oxo-dispiro-(5,1,11,2)-heneicosane
(140) 2,2,4,4-tetramethyl-20-butyl-7-oxa-3,20-diaza-21-oxo-dispiro-(5,1,11,2)-heneicosane
(141) 2,2,4,4-tetramethyl-20-iso-butyl-7-oxa-3,20-diaza-21-oxo-dispiro-(5,1,11,2)-heneicosane
(142) 2,2,4,4-tetramethyl-20-pentyl-7-oxa-3,20-diaza-21-oxo-dispiro-(5,1,11,2)-heneicosane
(143) 2,2,4,4-tetramethyl-20-hexyl-7-oxa-3,20-diaza-21-oxo-dispiro-(5,1,11,2)-heneicosane
(144) 2,2,4,4-tetramethyl-20-octyl-7-oxa-3,20-diaza-21-oxo-dispiro-(5,1,11,2)-heneicosane
(145) 2,2,4,4-tetramethyl-20-heptyl-7-oxa-3,20-diaza-21-oxo-dispiro-(5,1,11,2)-heneicosane
(146) 2,2,4,4-tetramethyl-20-octadecyl-7-oxa-3,20-diaza-21-oxo-dispiro(5,1,11,2)-heneicosane
(147) 2,2,4,4-tetramethyl-20-benzyl-7-oxa-3,20-diaza-21-oxo-dispiro-(5,1,11,2)-heneicosane
(148) 1',4'-bis-[2,2,4,4-tetramethyl-7-oxa-3,20-diaza-21-oxo-dispiro-(5,1,11,2)-heneicosyl-20-]-butane (149) 1',5'-bis-[2,2,4,4-tetramethyl-7-oxa-3,20-diaza-21-oxo-dispiro-(5,1,11,2)-heneicosyl-20-]-pentane (150) 1',6'-bis-[2,2,4,4-tetramethyl-7-oxa-3,20-diaza-21-oxo-dispiro-(5,1,11,2)-heneicosyl-20-]-hexane (151) 1',10'-bis-[2,2,4,4-tetramethyl-7-oxa-3,20-diaza-21-oxo-dispiro-(5,1,11,2)-heneicosyl-20-[decane (152) 2,2,4,4,21-pentamethyl-7-oxa-3,21-diaza-20-dispiro-(5,1,11,2)-heneicosane (153) 7,7,9,9-tetramethyl-2,2-dibenzyl-3-hexyl-1-oxa-3,8-diaza-4-oxo-spiro-(4,5)-decane (154) 7,7,9,9-tetramethyl-2,2-dibenzyl-3-octadecyl-1-oxa-3,8-diaza-4-oxo-spiro-(4,5)-decane (155) 7,7,9,9-tetramethyl-2,2,3-tribenzyl-1-oxa-3,8-diaza-4-oxo-spiro-(4,5)-decane (156) 1,2-bis-[2,2,7,7,9,9-hexamethyl-1-oxa-3,8-diaza-4-oxo-dispiro-(4,5)-decan-3-methyl-]-benzene.

The novel compounds are prepared according to the following reaction scheme from polyalkyl-1-oxa-diaza-spirodecanes of the formula (IV), which for their part are obtained according to German Pat. Nos. 2,606,026; 2,634,957 and 2,834,962, and halogen compounds of the formula (V), while hydrogen halide is split off:

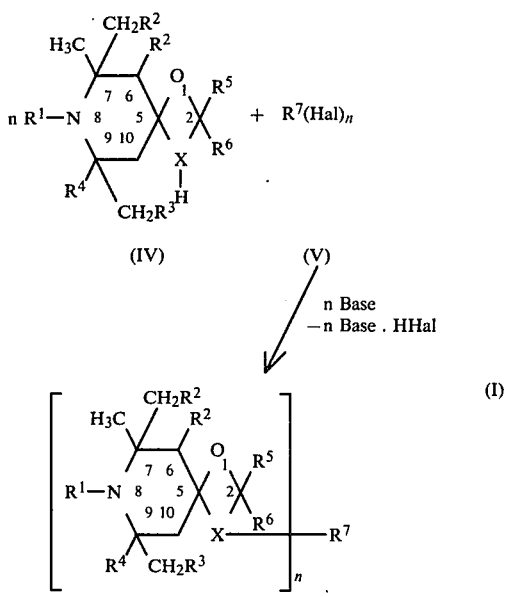

The radicals $R^1$ through $R^7$ and X are as defined above, Hal is chlorine, bromine or iodine, n is 1 or 2.

In detail, the following radicals are suitable:

$R^1$ = hydrogen, oxygen, methyl, butyl, hexyl, octyl, dodecyl $R^2$ = hydrogen, methyl, ethyl, butyl $R^3$ = hydrogen, methyl, ethyl, butyl $R^4$ = methyl $R^3$ and $R^4$ together with the carbon atom 9 = cyclohexyl, 2,2,6,6-tetramethylpiperidyl $R^5$ and $R^6$ = hydrogen, ethyl, propyl, iso-propyl, butyl, iso-butyl, pentyl, iso-pentyl, hexyl, iso-hexyl, heptyl, iso-heptyl, octyl, nonyl, iso-nonyl, decyl, undecyl, tridecyl, octadecyl, phenyl, 2,4-dichlorophenyl $R^5$ and $R^6$ together with the carbon atom 2 = cyclohexylidene, 3,5-dimethylcyclohexylidene, 3,3,5,5-tetramethylcyclohexylidene, cycloheptylidene, cyclododecylidene, 2,2,6,6-tetramethylpiperidylene $R^7$ = methyl, ethyl, propyl, butyl, pentyl, hexyl, heptyl, octyl, nonyl, dodecyl, tetradecyl, octadecyl, benzyl, ethylene, propylene, butylene, pentylene, hexylene, decylene, butenylene, xylylene.

The synthesis is carried out as follows: In the case where n is 1, the compounds (IV) and (V) are reacted with each other in a molar ratio of from 1:1 to 1:10, preferably 1:1.2 to 1:5, especially 1:1.5 to 1:3; and in the case where n is 2, in a molar ratio of from 2.5:1 to 2:1, preferably 2.1:1 to 2:1, especially 2:1. The reaction is performed in an organic solvent in the presence of an equimolar to 20-fold amount of solid alkali metal hydroxide, or a 20% to, preferably, 50%, aqueous alkali metal hydroxide solution in the presence of a phase transfer catalyst. The reaction temperature is in the range of from 20° to 120° C., preferably 20° to 70° C., especially 40° to 60° C. As organic solvents, there are used aliphatic or aromatic hydrocarbons such as petroleum ether, hexane, heptane, gasoline fractions, toluene, cyclohexane etc., or an excess of alkyl halide. By phase transfer catalysts, there are to be understood compounds selected from the group of quaternary ammonium halides, which are employed in an amount of from 0.1 to 5 weight %, relative to compound (IV); tricaprylmethylammonium chloride being especially suitable. The reaction is generally complete after 1 to 20 hours, depending on the reactivity of the halogen component.

For work-up, the phases are separated, optionally after addition of a small amount of water. The organic phase is repeatedly washed with water, dried over $Na_2SO_4$ or $MgSO_4$, concentrated, and the residue is recrystallized. In some cases, the final products crystallize already in the reaction solutions and are then isolated by filtration.

It was surprising and not to be expected that especially those compounds in which $R^1$ is H could be prepared according to the above method. In contrast to the course of reaction actually observed and proved by $^{13}$C-NMR examination, a substitution at the piperidine nitrogen was rather to be calculated on, because due to its higher basicity its nucleophilic power is considerably greater than that of amide nitrogen in the atom group X.

As to properties and efficiency of the novel compounds, it should have been expected that there are no differences at all or to an insignificant extent only as compared with 1-oxa-diaza-spirodecanes of similar structure described in the patent literature and recommended as plastics stabilizers (German Offenlegungsschriften Nos. 1,770,689 and 2,227,689). Surprisingly, however, the novel compounds are highly superior to even the best of the compounds listed in the above German Offenlegungsschriften, that is, that of Example 58 of German Offenlegungsschrift No. 1,770,689. This compound, namely 7,7,8,9,9-pentamethyl-3-epoxypropyl-1,3,8-triaza-spiro-(4,5)-decane-2,4-dione, although distinguished by a very good stabilizing action, is highly volatile on processing. This is valid, too, for the compounds of German Offenlegungsschriften Nos. 2,606,026 and 2,634,957, and they can be easily washed off from the thermoplastic materials containing them.

High-quality stabilizers, however, have to meet severe requirements in addition to their stabilizing action, especially with respect to the above physical properties. For, a too high volatility results in considerable stabilizer losses on processing of the polymers, and the activity of the stabilizer is reduced when it is too readily washed off, for example on sprinkling with water.

It was therefore not to be expected at all that, despite their relationship with the compounds of the cited Offenlegungsschriften, the compounds of the invention are not only more effective as stabilizers, but also excel by an especially low volatility and increased resistance to being washed off (these advantageous properties being present above all in the compounds where n is 2), so that this must be considered as an essential technical progress.

As already mentioned, the novel compounds are used as stabilizers for plastic materials against damage thereof by influence of oxygen, heat and light. Examples of those plastics are the following:

Polymers which are derived from hydrocarbons with one or two unsaturated olefinic bonds, for example polyolefins such as polyethylene, optionally cross-linked, polypropylene, polybutene-1, polyisobutene, polymethylbutene-1, polymethylpentene-1, polyisoprene, polybutadiene, polystyrene, copolymers of the monomers on which the abovementioned homopolymers are based, such as ethylene/propylene copolymers propylene/butene-1 copolymers, propylene/isobutene copolymers, styrene/butadiene copolymers, as well as terpolymers of ethylene and propylene with a diene, such as hexadiene, dicyclopentadiene or ethylidene-norbornene, mixtures of the abovementioned homopolymers, for example mixtures of polypropylene and polyethylene, polypropylene and polybutene-1, polypropylene and polyisobutylene, or of a butadiene/acrylonitrile copolymer with a styrene/butadiene copolymer.

Vinyl polymers containing halogen, such as polyvinyl chloride, polyvinylidene chloride, polyvinyl fluoride, polychloroprene and chlorinated rubber, as well as copolymers of vinyl chloride and vinylidene chloride with one another and with other olefinically unsaturated monomers.

Polymers derived from $\alpha,\beta$-unsaturated acids and their derivatives, such as polyacrylates, polymethacrylates, polyacrylamides and polyacrylonitrile, as well as their copolymers with one another and with other vinyl compounds, for example acrylonitrile/butadiene/styrene, acrylonitrile/styrene and acrylonitrile/styrene/acrylic ester copolymers.

Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

Homopolymers and copolymers which are derived from epoxides, such as polyethylene oxide or polymers derived from bisglycidyl ethers.

Polyacetals, such as polyoxymethylene and polyoxyethylene, as well as those polyoxymethylenes which contain ethylene oxide as comonomer.

Polyurethane and polyureas.

Polycarbonates.

Polyamides and copolyamides derived from diamines and dicarboxylic acids and/or from aminocarboxylic acids or the corresponding lactatms, such as polyamide 6, polyamide 6/6, polyamide 6/10, polyamide 11, polyamide 12.

Polyesters derived from dicarboxylic acids and diols and/or from hydroxy carboxylic acids or from the corresponding lactones, such as polyethylene glycol terephthalate, polybutyleneterephthalate, poly-1,4-dimethylol-cyclohexaneterephthalate.

Cross-linked polymers which on the one hand are derived from aldehydes and on the other hand from phenols, ureas and melamines, such as phenol/formaldehyde, urea/formaldehyde and melamine/formaldehyde resins.

Of special importance is the stabilization of polyolefins, styrene polymers, polyamides, poly-(meth-)acrylates and of polyurethanes, for which the novel compounds are especially suitable. Examples thereof are polyethylene of higher and lower density, polypropylene, ethylene/propylene copolymers, polystyrene, styrene/butadiene/acrylonitrile terpolymers, mixtures of polyolefins or of styrene polymers, polyurethanes on the basis of polyether or polyester in the form of lacquers, fibers, sheets, plates, films, elastomers or foam plastics.

The new stabilizers are incorporated into the polymer masses according to the methods generally used. The incorporation can be carried out, for example, by intermixing the compounds and optionally other additives with the melt according to the methods usual in the industrial practice, before or during shaping, or also by applying the dissolved or dispersed compounds directly to the polymer, or by intermixing them with a solution, suspension or emulsion of same, optionally with subsequently allowing the solvent to evaporate. The amounts are from 0.01 to 5, preferably 0.05 to 2.5, and especially 0.1 to 1.0% by weight, relative to the material to be stabilized. The new compounds can also be added to the plastics to be stabilized in the form of a masterbatch containing these compounds, for example in a concentration of from 2.5 to 50, preferably 5.0 to 20, % by weight.

The plastics stabilized by addition of substances of formula (I) may contain other known and usual additives such as antioxidants based on phenol and sulfide, UV absorbers and light protecting agents, phosphite stabilizers, metal compounds, epoxy stabilizers and polyalcohols.

Examples of antioxidants are those of the type of sterically hindered phenols, such as 4,4'-butylidene-bis-(2,6-di-t.-butyl-phenol), 4,4'-thio-bis-(2-t.-butyl-5-methyl-phenol), phenolic triazine compounds, thiodipropionic acid esters of fatty alcohols, dioctadecyl sulfide and -disulfide.

The UV-absorbers and light protecting agents include, for example, 2-(2'-hydroxyphenyl)-benzotriazoles, such as 2-(2'-hydroxy-5'-methylphenyl)-benzotriazole, 2-hydroxybenzophenones, such as 2-hydroxy-4-octoxy-benzophenone, stabilizers of the group of the salicylates, such as octylphenyl salicylate, nickel chelates, oxalic acid diamides and sterically hindered piperidine compounds.

As phosphites there are to be mentioned trisnonylphenyl phosphite, trislauryl phosphite and esters of pentaerythritol phosphite.

By metal compounds known as stabilizers there are to be understood: Calcium, barium, strontium, zinc, cadmium, magnesium, aluminum and lead soaps of aliphatic carboxylic acids or hydroxycarboxylic acids having about 12 to 32 carbon atoms, salts of the aforesaid metals with aromatic carboxylic acids, such as benzoates or salicylates, and (alkyl-)phenolates of these metals, and also organo-tin compounds such as, for example, dialkyltin thioglycolates and carboxylates.

Known epoxy stabilizers are, for example, epoxidized higher fatty acids, such as epoxidized soybean oil, tall oil, linseed oil or epoxidized butyl oleate, and also epoxides of long-chain olefins.

Polyols may be, for example, pentaerythritol, trimethylolpropane, sorbitol or mannitol, i.e. preferably alcohols having 5 or 6 carbon atoms and 3 to 6 OH-groups.

An effective stabilizer combination for poly-α-olefins such as, for example, high, medium and low pressure polymers of $C_2$- to $C_4$-α-olefins, especially polyethylene and polypropylene or copolymers of such α-olefins, consists, calculated on 100 parts by weight of polymer, for example, of from 0.01 to 5 parts by weight of one of the compounds to be used in accordance with the invention, of from 0.05 to 5 parts by weight of a phenolic stabilizer, optionally of from 0.01 to 5 parts by weight of a sulfur-containing costabilizer, and optionally of from 0.01 to 3 parts by weight of a basic or neutral metal soap such as, for example, calcium stearate or zinc stearate, and optionally of from 0.1 to 5 parts by weight of a phosphite and optionally of from 0.01 to 5 parts by weight of a known UV-stabilizer of the group of alkoxy-hydroxybenzophenones, 4-hydroxyphenyl-benzotriazoles, benzylidene-malonic acid-mononitrile esters or the so-called quenchers, such as nickel chelates.

The plastics stabilized according to the invention can be used in most different shapes, for example as sheets, fibers, ribbons, profiles, or as binders for laquers, adhesives or cements.

The following examples illustrate the invention.

EXAMPLE 1

2,2,4,4,7,7,9,9-heptamethyl-1-oxa-4,8-diaza-3-oxo-spiro-(4,5)-decane (Compound No. 14)

6.8 g of 2,2,7,7,9,9-hexamethyl-1-oxa-4,8-diaza-3-oxo-spiro-(4,5)-decane and 20 g of methyl iodide were introduced into the reactor in 50 ml of toluene. After having added three drops of the phase transfer catalyst tricaprylmethylammonium chloride, 20 ml of 50% sodium hydroxide solution were added to the reaction mixture, and it was agitated for 5 hours at 45° C. During the reaction, the batch becomes first jelly and then transparent. The phases are subsequently separated and the organic phase is shaken twice with 30 ml each of water, filtered and concentrated. The residue is recrystallized from petroleum ether. 5.4 g of white crystals/m.p. 128°–130° C.

The same results are obtained when operating in hexane, heptane and cyclohexane as solvent.

EXAMPLES 2 TO 71

Operations were as described in Example 1 with the use of other educts.

Test conditions and characteristics of the products are listed in the following Table. Column 2 (Compound No.) indicates the compounds cited pages 4 to 13.

| Ex. No. | Comp. No. | Starting materials Polyalkyl-1-oxa-diaza-spiro-decane; amount (g) | Halogen compound amount (g) | Base (ml) | Reaction time (hours) | Temperature (°C.) | Recryst. from | M.p. (°C.) |
|---|---|---|---|---|---|---|---|---|
| 2 | 9 | 2,2,7,7,9,9-Hexamethyl-1-oxa-3,8-diaza-4-oxo-spiro-(4,5)-decane (20) | 1-Bromo-octadecane (28) | 50% NaOH (7) | 13 | 80 | Petrol ether | 117 |
| 3 | 10 | idem (20) | Benzyl chloride (11) | idem (7) | 16 | 80 | Heptane | 119 |
| 4 | 13 | idem (9) | 1,10-Dibromo-decane (5,7) | idem (8) | 16 | 50 | Ether | 136–142 |
| 5 | 12 | idem (9) | 1,6-Dibromo-hexane (4,6) | idem (8) | 16 | 50 | Petrol ether | 136–142 |
| 6 | 4 | idem (9) | 1-Bromo-butane (20) | idem (20) | 5 | 55 | idem | 50–53 |
| 7 | 6 | idem (12) | 2-Bromo-hexane (30) | idem (20) | 6 | 50 | idem | 30–33 |
| 8 | 22 | 2,2,7,7,9,9-Hexamethyl-1-oxa-3-oxo-4,8-diaza-spiro-(4,5)-decane (8,5) | 1,6-Dibromo-hexane (4) | KOH (2) | 24 | 55 | Hexane | 145 |
| 9 | 16 | idem (7) | Iodine ethane (20) | 50% NaOH (20) | 6 | 55 | Heptane | 82–84 |
| 10 | 21 | idem (6) | Benzyl chloride (30) | idem (20) | 8 | 55 | idem | 133–136 |
| 11 | 20 | idem (6) | 1-Bromo-octa-decane (18) | idem (20) | 16 | 55 | Petrol ether | 50–52 |
| 12 | 18 | 2,2,7,7,9,9-Hexamethyl-1-oxo-3-oxo-4,8-diaza-spiro-(4,5)-decane (8,5) | 1-Bromo hexane (30) | 50% NaOH (20) | 7 | 50 | Petrol ether | 57–58 |
| 13 | 29 | 2,7,7,9,9-Pontamethyl-2-ethyl-1-oxa-3-oxo-4,8-diaza-spiro-(4,5)-decane (7,8) | idem (4) | idem (5) | 6 | 80 | Heptane | 71 |
| 14 | 30 | idem (4,8) | Benzyl chloride (10) | idem (5) | 6 | 60 | idem | 108 |
| 15 | 15 | 2,2,7,7,8,9,9-Hepta-methyl-1-oxa-4,8-diaza-spiro-(4,5)-decane (7) | 1-Bromo-butane (25) | idem (25) | 6 | 55 | idem | 58 |
| 16[1] | 33 | 2,7,7,9,9-Pentamethyl-2-propyl-1-oxa-3,8-diaza-4-oxo-spiro-(4,5)-decane (3,4) | Iodine-ethane (20) | idem (5) | 5 | 60 | Heptane | 101 |
| 17 | 34 | idem (6,6) | 1,4-Dibromo-butane (2,7) | idem (5) | 20 | 60 | idem | 142 |
| 18 | 36 | 2,7,7,9,9-Pentamethyl-2-iso-propyl-1-oxa-3-oxo-4,8-diaza-spiro-(4,5)-decane (8) | 1-Bromo-hexane (20) | idem (20) | 6 | 60 | Hexne | 90 |
| 19 | 38 | 2,7,7,9,9-Pentamethyl- | Iodine ethane | 50% | 6 | 50 | Hexane | 105– |

-continued

| Ex. No. | Comp. No. | Starting materials Polyalkyl-1-oxa-diaza-spiro-decane; amount (g) | Halogen compound amount (g) | Base (ml) | Reaction time (hours) | Temperature (°C.) | Recryst. from | M.p. (°C.) |
|---|---|---|---|---|---|---|---|---|
|  |  | 2-iso-propyl-1-oxa-3-oxo-4,8-diaza-spiro-(4,5)-decane (8) | (20) | NaOH (5) |  |  |  | 107 |
| 20[2] | 47 | 2,7,7,9,9-Pentamethyl-2-butyl-1-oxa-3-oxo-4,8-diaza-spiro-(4,5)-decane (7) | idem | idem (20) | 6 | 55 | Heptane | 57 |
| 21[2] | 50 | 2,7,7,9,9-Pentamethyl-2-pentyl-1-oxa-3,8-diaza-4-oxo-spiro-(4,5)-decane (3,6) | Benzyl chloride (4) | idem (10) | 6 | 70 | idem | 81 |
| 22 | 53 | 2,7,7,9,9-Pentamethyl-2-pentyl-1-oxa-3-oxo-4,8-diaza-spiro-(4,5)-decane (4) | idem (2) | idem (5) | 6 | 65 | idem | 56 |
| 23 | 64 | 2,7,7,9,9-Pentamethyl-2-iso-hexyl-1-oxa-3-oxo-4,8-diaza-spiro-(4,5)-decane (5,8) | idem (10) | idem (7) | 5 | 60 | Petrol ether | 30 |
| 24 | 63 | 2,7,7,9,9-Pentamethyl-2-hexyl-1-oxa-3-oxo-4,8-diaza-spiro-(4,5)-decane (6,2) | 1-Bromo-octa-decane (10) | idem (7) | 24 | 55 | — | wax |
| 25 | 62 | 2,7,7,9,9-Pentamethyl-2-hexyl-1-oxa-3-oxo-4,8-diaza-spiro-(4,5)-decane (10) | 1,6-Dibromo-hexane (4) | 50% NaOH (5) | 24 | 50 | Hexane | 120 |
| 26 | 61 | idem (10) | 1,4-Dibromo-butane (3,5) | idem (8) | 24 | 50 | Heptane | 128–132 |
| 27 | 60 | idem (8) | 1-Bromo-hexane | idem (20) | 8 | 60 | — | Wax |
| 28 | 58 | idem (8) | Bromo-ethane (20) | idem (20) | 6 | 40 | — | Wax |
| 29 | 59 | 2,7,7,9,9-Pentamethyl-2-hexyl-1-oxa-3-oxo-4,8-diaza-spiro-(4,5)-decane (8) | 1-Bromo-butane (20) | idem (20) | 8 | 50 | — | Wax |
| 30 | 65 | 2,7,7,9,9-Pentamethyl-2-nonyl-1-oxa-3,8-diaza-4-oxo-spiro-(4,5)-decane (8) | Bromo-hexane (20) | idem (20) | 8 | 45 | Petrol ether | 39–44 |
| 31 | 72 | 2,7,7,9,9-Pentamethyl-2-undecyl-1-oxa-3,8-diaza-4-oxo-spiro-(4,5)-decane (5) | 1-Bromo-hexane (20) | idem (5) | 10 | 55 | — | Oil |
| 32[2] | 76 | 2,7,7,9,9-Pentamethyl-2-Undecyl-1-oxa-3,8-diaza-4-oxo-spiro-(4,5)-decane (7,6) | 1,6-Dibromo-hexane (2,5) | 50% NaOH (10) | 8 | 60 | Petrol ether | 25 |
| 33 | 79 | 2,7,7,9,9-Pentamethyl-2-undecyl-1-oxa-3-oxo-4,8-diaza-spiro-(4,5)-decane (4) | Benzyl chloride (4) | idem (5) | 6 | 75 | idem | 36 |
| 34[1] | 82 | 2,7,7,9,9-Pentamethyl-2-octadecyl-1-oxa-3,8-diaza-4-oxo-spiro-(4,5)-decane (6) | iodine methane (20) | idem (8) | 6 | 40 | — | 48–50 |
| 35 | 89 | 7,7,9,9-Tetramethyl-2,2-diethyl-1-oxa-3,8-diaza-4-oxo-spiro-(4,5)-decane (6) | Bromo-ethane (20) | idem (20) | 8 | 50 | Petrol ether | 102–105 |
| 36 | 90 | idem (6) | 1-Bromo-butane (20) | idem (20) | 8 | 50 | idem | 85–90 |
| 37 | 91 | idem (7) | 1-Bromo-hexane (20) | idem (20) | 8 | 55 | idem | 70–71 |
| 38 | 92 | idem (6) | Benzyl chloride (10) | idem (20) | 8 | 55 | idem | 111–115 |
| 39 | 90 | 7,7,9,9-Tetramethyl-2,2-diethyl-1-oxa-3,8-diaza-4-oxo-spiro-(4,5)-decane (6,7) | 1,6-Dibromo-hexane (3,3) | 50% NaOH (20) | 20 | 50 | Petrol ether | 126 |
| 40[2] | 97 | 7,7,9,9-Tetramethyl-2-ethyl-2-butyl-1-oxa-3-oxo-4,8-diaza-spiro-(4,5)-decane (5,0) | Benzyl chloride (5) | idem (5) | 8 | 55 | Heptane | 75–77 |
| 41 | 99 | 7,7,9,9-Tetramethyl-2,2-dibutyl-1-oxa-3-oxo-4,8-diaza-spiro-(4,5)-decane (2) | idem (2) | idem (3) | 8 | 55 | idem | 49 |
| 42 | 105 | 7,7,9,9-Tetramethyl-2,2-dipentyl-1-oxa- | 1,10-Dibromo-pentane (7,5) | KOH (3) | 24 | 50 | Petrol ether | 40–45 |

-continued

| Ex. No. | Comp. No. | Starting materials Polyalkyl-1-oxa-diaza-spiro-decane; amount (g) | Halogen compound amount (g) | Base (ml) | Reaction time (hours) | Temperature (°C.) | Recryst. from | M.p. (°C.) |
|---|---|---|---|---|---|---|---|---|
| | | 3,8-diaza-4-oxo-spiro-(4,5)-decane (17,6) | | | | | | |
| 43 | 103 | idem (17,6) | 1,4-Dibromo-butane (5,4) | idem (3) | 24 | 50 | idem | 89–96 |
| 44 | 102 | idem (5,5) | Benzyl chloride (5) | 50% NaOH (10) | 10 | 60 | idem | 58 |
| 45 | 101 | idem (5,5) | 1-Bromo-octadecane (10) | idem (10) | 20 | 70 | — | Wax |
| 46 | 153 | 7,7,9,9-Tetramethyl-2,2-dibenzyl-1-oxa-3,8-diaza-4-oxo-spiro-(4,5)-decane (7) | 1-Bromo-hexane (15) | 50% NaOH (7) | 10 | 65 | Heptane | 122 |
| 47 | 154 | idem (7) | 1-Bromo-octadecane (15) | idem (7) | 7 | 65 | — | Wax |
| 48 | 155 | idem (7) | Benzyl chloride (10) | idem (7) | 7 | 65 | Heptane | 192 |
| 49 | 113 | 7,7,9,9-Tetramethyl-2-iso-propyl-1-oxa-3-oxo-4,8-diaza-spiro-(4,5)-decane (7,3) | Bromo-ethane (20) | idem (20) | 8 | 50 | Petrol ether | 68–72 |
| 50[1] | 114 | 7,7,9,9-Tetramethyl-2-iso-hexyl-1-oxa-3-oxo-4,8-diaza-spiro-(4,5)-decane (1) | Bromo-ethane (20) | idem (2) | 8 | 40 | idem | 35–40 |
| 51[1] | 123 | 2,2,4,4-Tetramethyl-7-oxa-3,13-diaza-14-oxo-dispiro-(5,1,4,2)-tetradecane (7) | 1-Bromo-hexane (30) | idem (20) | 6 | 50 | idem | 74–76 |
| 52 | 124 | idem (8,5) | Bromo-ethane (20) | idem (20) | 5 | 50 | idem | 79–81 |
| 53[3] | 125 | 2,2,4,4-Tetramethyl-7-oxa-3,13-diaza-14-oxo-dispiro-(5,1,4,2)-tetradecane (8) | 1-Bromo-butane (20) | 50% NaOH (20) | 5 | 50 | Petrol ether | 65–70 |
| 54[3] | 131 | 2,2,4,4-Tetramethyl-7-oxa-3,14-diaza-15-oxo-dispiro-(5,1,5,2)-pentadecane (28) | 1,4-Dichloro-butane (6) | idem (50) | 24 | 70 | idem | Wax |
| 55 | 132 | idem (28) | 1,6-Dibromo-hexane (10) | idem (50) | 24 | 70 | — | idem |
| 56[1] | 136 | 2,2,4,4-Tetramethyl-7-oxa-3,15-diaza-14-oxo-dispiro-(5,1,5,2)-pentadecane (7) | 1-Bromo-hexane (20) | idem (20) | 5 | 50 | Petrol ether | 63–65 |
| 57[1] | 134 | 2,2,4,4,10,10,12,12-Octamethyl-7-oxa-3,14-diaza-15-oxo-dispiro-(4,1,5,2)-pentadecane (2,5) | Iodine ethane (10) | idem (4) | 5 | 55 | Heptane | 198 |
| 58[3] | 137 | 2,2,4,4-Tetramethyl-7-oxa-3,20-diaza-21-oxo-dispiro-(5,1,11,2)-heneicosane (18,2) | Iodine methane (20) | idem (30) | 8 | 45 | idem | 179–181 |
| 59[3] | 138 | idem (10) | Bromo-ethane (20) | idem (20) | 8 | 60 | Hexane | 159–160 |
| 60[3] | 139 | 2,2,4,4-Tetramethyl-7-oxa-3,20-diaza-21-oxo-dispiro-(5,1,11,2)-heneicosane (18,5) | 2-Bromo-propane (20) | 50% NaOH (20) | 8 | 55 | Heptane | 141 |
| 61[3] | 140 | idem (10) | 1-Bromo-butane (20) | idem (20) | 8 | 60 | Hexane | 124–126 |
| 62[3] | 141 | idem (18,2) | 2-Bromo-butene (20) | idem (20) | 8 | 60 | idem | 128–130 |
| 63[3] | 143 | idem (18,2) | 1-Bromo-hexane (20) | idem (20) | 8 | 60 | idem | 77–81 |
| 64[3] | 142 | idem (18,2) | 1-Bromo-pentane (20) | idem (20) | 8 | 60 | idem | 122 |
| 65[3] | 144 | idem (18,2) | 1-Bromo-octane (20) | idem (20) | 8 | 60 | idem | 80 |
| 66[3] | 145 | idem (18,2) | 1-Bromo-heptane (20) | idem (20) | 8 | 60 | idem | 88 |
| 67[3] | 147 | idem (18,2) | Benzyl chloride (20) | idem (20) | 8 | 60 | Heptane | 155 |
| 68[3] | 149 | idem (18,2) | 1,5-dibromo-pentane (5,7) | idem (40) | 20 | 50 | idem | 188 |
| 69[3] | 150 | 2,2,4,4-Tetramethyl-7-oxa-3,20-diaza-21-oxo-dispiro-(5,1,11,2)-henicosane (18,2) | 1,6-Dibromo-hexane (6,1) | 50% NaOH (40) | 20 | 50 | Heptane | 198 |

-continued

| Ex. No. | Comp. No. | Starting materials Polyalkyl-1-oxa-diaza-spiro-decane; amount (g) | Halogen compound amount (g) | Base (ml) | Reaction time (hours) | Temperature (°C.) | Recryst. from | M.p. (°C.) |
|---|---|---|---|---|---|---|---|---|
| 70[3] | 151 | idem (36,4) | 1,10-Dibromo-decane (15) | idem (40) | 20 | 50 | Heptane | 155 |
| 71 | 156 | 2,2,7,7-hexamethyl-1-oxa-3,8-diaza-4-oxo-dispiro-(4,5)-decane (26,2) | 1,2-Bis-(chloro-naphthyl)-benzene (8,8) | idem (30) | 30 | 60 | Petrol-ether | 102–104 |

[1] without solvent
[2] 20 ml Toluene as solvent
[3] 150 ml Toluene as solvent

EXAMPLE 72

This example shows the volatility of the stabilizers in accordance with the invention as compared to products of the state of the art according to German Offenlegungsschrift No. 2,227,689.

The volatility values were determined in an apparatus for thermogravimetric analysis. Identical amounts (500 mg) each of the stabilizers of the invention and of the comparative substances were heated at a speed of 2 K/min to 300° C. in a nitrogen atmosphere, and the loss of substance was measured in mg/cm$^2$. The results are indicated in the following Table:

| Stabilizer acc. to Example | weight losses in mg/cm$^2$ when attaining ... °C. | | | |
|---|---|---|---|---|
| | 200 | 260 | 300 | 10 min at 300 |
| 5 | 0.63 | 4.11 | 14.85 | 24.33 |
| 4 | 0.79 | 3.63 | 13.27 | 20.22 |
| 2 | 1.58 | 7.43 | 22.44 | 35.39 |
| 69 | 0.32 | 2.37 | 7.27 | 11.06 |
| 70 | 0.01 | 0.32 | 2.05 | 3.79 |
| comparison[1] | 14.06 | 45.82 | 148.62 | 153.26 |

[1] Compound according to Example 58 of German Offenlegungsschrift No. 2,227,689.

EXAMPLE 73

For testing the stabilizing properties of the novel compounds, operations were as follows:

100 Parts by weight of polypropylene having a melt flow index is of about 6 g/10 min (determined according to ASTM D 1238-62 T) and a density of 0.90 were mixed with 0.1 part by weight of pentaerythrityl-tetrakis-3-(3,5-di-tert.-butyl-4-hydroxyphenyl)-propionate, 0.2 part by weight of calcium stearate, and 0.3 part by weight of the stabilizer of the invention to be examined.

In order to obtain a distribution as uniform as possible on the polymer grain, the stabilizers were dissolved in a solvent, and the solution was added dropwise to the polypropylene powder with agitation, while the substantial part of the solvent was evaporated by simultaneous radiation with an IR lamp. After about 20 minutes, the calcium stearate was added, and mixing was continued for another 10 minutes. Solvent residues were removed by drying at 50° C./120 min in a drying cabinet.

On a Windsor injection molding machine type SP 50, the polypropylene was injection-molded at 240° C. to plates having dimensions of 60×60×1 mm, from which plates test specimens according to German Industrial Standard DIN 53 455, form 3, were cut in a reduced scale of 1:3. The test specimens required for comparison were manufactured in analogous manner, but without the stabilizer to be tested or with addition of the comparative stabilizers.

For determining the stability to light, the specimens were exposed to radiation with light intensity variation of a Xenotest-1200 apparatus of the company Original Hanau Quarzlampen GmbH. The radiation intensity was modulated by UV filters (special filter glass d=1.7 mm). The stability to light was tested according to German Industrial Standard DIN No. 53 387 (17 minutes of moistening, 3 minutes of sprinkling, blackpanel temperature 45° C., atmospheric moisture 70–75%). The time of exposure was measured in hours, and the elongation at break was determined on a tensile testing machine of the Instron company at a draw-off speed of 5 cm/min.

| Stabilizer acc. to Example | Exposure time hours | elongation at break in % of initial value |
|---|---|---|
| 5 | 1 100 | >50 |
| 4 | 1 100 | >50 |
| 2 | 1 100 | >50 |
| 69 | 1 100 | >50 |
| 70 | 1 100 | >50 |
| Polypropylene Comparison (without stabilizer) | 260 320 | 1 1 |
| Comparison[1] | 1 100 | 2 |

[1] Compound according to Example 58 of German Offenlegungsschrift No. 2,227,689.

EXAMPLE 74

0.26 part by weight of the stabilizers indicated below are mixed by means of a laboratory high-speed mixer with polypropylene (Hostalen PPU VP 1770 F of Hoechst AG) having a melt flow index MFI 190/51.9 g/10 min according to German Industrial Standard No. DIN 53 535. The material so stabilized was melted in a laboratory extruder under usual processing conditions, and processed via a spinning pump having a multiple spinneret to give monofilaments (87 dtex), which were subsequently after-drawn in a ratio of 1:2.5. 24 each of these filaments were texturized to give a yarn which was processed to test fabrics. The specimens were subjected to a light fastness test in a fadeometer and, after the time of exposure as indicated, subjected to a finger nail test (light rubbing with the thumb nail over the fabric). The degree of degradation is expressed in numbers (0=no damage, 1 to 5=increasing destructibility).

| Stabilizer acc. to Example (p.b.w.) | Destructibility of fabric after ... hours of exposure | | |
|---|---|---|---|
| | 40 | 80 | 160 |
| without stab. (Comp.) | 0 | 0 | 5 |
| 5 | 0 | 0 | 0 |

| Stabilizer acc. to Example (p.b.w.) | Destructibility of fabric after ... hours of exposure | | |
|---|---|---|---|
| | 40 | 80 | 160 |
| 4 | 0 | 0 | 0 |
| 2 | 0 | 0 | 0 |
| 69 | 0 | 0 | 0 |
| 70 | 0 | 0 | 0 |
| Comparison[1] | 0 | 0 | 1 |

[1]Compound according to Example 58 of German Offenlegungsschrift No. 2,227,689.

What is claimed is:

1. A polyalkyl-diaza-spirodecane of the formula

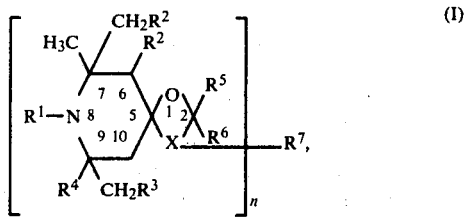

(I)

in which

X stands for a group of the formulae (II) or (III)

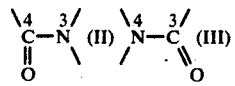

the indices 3 and 4 indicating the ring positions in the diaza-spirodecane system, and the free valancy of the nitrogen atom producing the linkage with $R^7$;

$R^1$ is hydrogen, oxygen or $C_1$–$C_{12}$-alkyl, $R^2$ and $R^3$ either are identical and represent hydrogen or a $C_1$–$C_4$-alkyl group, in which case $R^4$ is a methyl group; or $R^2$ is hydrogen or $C_1$–$C_5$-alkyl; and $R^3$ and $R^4$, together with the carbon atoms to which they are linked, form a $C_5$- and $C_6$-cycloalkyl group or a group of the formula

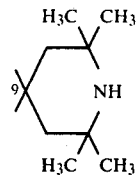

$R^5$ and $R^6$ are identical or different and represent hydrogen, $C_1$–$C_{30}$-alkyl, an unsubstituted phenyl or naphthyl group or a phenyl or naphthyl group substituted by chlorine or $C_1$–$C_4$-alkyl, or an unsubstituted $C_7$–$C_{12}$-phenylalkyl group or such a group substituted by $C_1$–$C_4$-alkyl, or $R^5$ and $R^6$, together with the carbon atom linking them, form an unsubstituted $C_5$–$C_{18}$-cycloalkyl group or such a group substituted by up to four $C_1$–$C_4$-alkyl groups, or a group of the formula

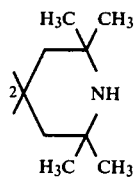

n is 2, and $R^7$ is an alkylene group having from 2 to 30 carbon atoms, an alkenylene group having from 2 to 30 carbon atoms, or a phenyldialkylene group having from 8 to 18 carbon atoms;

and their salts with non-oxidizing mineral acids, aliphatic sulfonic or phosphonic acids, aliphatic mono-, di- or polycarboxylic acids, or aromatic mono- or polycarboxylic acids.

* * * * *